United States Patent [19]

Collins

[11] 4,312,994

[45] Jan. 26, 1982

[54] α CHAIN DIENIC PROSTANOIC ACID DERIVATIVES

[75] Inventor: Paul W. Collins, Deerfield, Ill.

[73] Assignee: G. D. Searle & Co., Skokie, Ill.

[21] Appl. No.: 247,453

[22] Filed: Mar. 25, 1981

[51] Int. Cl.$^3$ ............................................. C07C 177/00
[52] U.S. Cl. .................................... 560/121; 560/118; 562/500; 562/503; 424/305; 424/317; 260/408; 260/410.9 R; 260/413
[58] Field of Search ................ 560/121, 118; 562/503, 562/500; 260/408, 410.9 R, 413

[56] References Cited

U.S. PATENT DOCUMENTS 4,087,620  5/1978  Hayashi ................................. 560/121
4,191,699  3/1980  Floyd et al. ................ 260/448.2 D

*Primary Examiner*—Robert Gerstl
*Attorney, Agent, or Firm*—James G. Passé

[57] ABSTRACT

α Diene 16-hydroxy prostanoic acid derivatives displaying valuable pharmacological properties, e.g., gastric antisecretory, are described herein.

19 Claims, No Drawings

α CHAIN DIENIC PROSTANOIC ACID DERIVATIVES

BACKGROUND OF INVENTION

The present invention relates to certain novel organic compounds. In particular this invention relates to certain novel prostanoic acid derivates of formula I on Chart A.

The novel compounds of the present invention display valuable pharmacological properties as is exemplified by their ability to inhibit the gastric secretion stimulated by secretogogues such as histamine and pentagastrin. In addition, these compounds possess the remarkable ability to protect the gastric mucosa against the damaging effects of such agents as ethanol and aspirin. This effect has been termed cytoprotection (see A. Robert et al Gastroenterology 77 433 (1979). Furthermore these compounds have the surprising advantage of lacking the potent undesirable side effects such as diarrhea and uterine stimulant activity displayed by related substances. The gastric antisecretory activity is determined by standard laboratory means.

Gastric antisecretory agents may be used to treat such diseases as hypersecretion of gastric acid and peptic ulcer. A number of methods to control these conditions exist including, gastric antacids, antimuscarinic drugs, $H_2$-receptor blockers and prostaglandins (PGE). Goodman and Gilman, Sixth Ed. 1980 pgs. 997, 632, 995–997 and 678.

PGE analogs are all known to cause side effects, notably diarrhea. However, the capacity to suppress gastric secretion by these compounds is well documented.

Prostanoic acid is well known and has the structure and numbering of formula II on Chart A.

The compounds are more particularly derivatives of $PGE_1$, which is obtained from mammalian tissues. For background on prostaglandins, see for example Bergstrom et al., Pharmacol Rev. 20, 1 (1968). For related compounds see Pace-Asciak et al., Biochem. 10, 3657 (1971).

PRIOR ART

Pharmacologically active prostanoic acid derivatives are well known in the art as indicated above, for a wide range of uses. U.S. Pat. No. 3,965,143 describes certain 16, oxygenated prostanoic acid derivatives displaying gastric antisecretory properties.

SUMMARY OF THE INVENTION

The present invention particularly provides a compound according to formula I: wherein n is an integer from 1 through 3 inclusive; wherein m+p are integers from 0 through 2 inclusive, m and p being either the same or different; wherein q is an integer of from 2 through 4 inclusive; wherein X and Y are cis or trans vinylene, X and Y being either the same or different; wherein R is:
  (a) hydrogen
  (b) alkyl of 1 to 6 carbon atoms inclusive;
wherein $R_1$ is:
  (a) hydrogen
  (b) alkyl of 1 to 6 carbon atoms inclusive;
  (c) vinyl
  (d) ethynyl
  (e) cyclopropyl
  (f) $-CH_2Z$
  (g) $-CH(Z)_2$
  (h) $-CZ_3$
wherein Z is:
  (a) chlorine
  (b) fluorine; and
wherein the ($\pm$) refers to the structure of formula I, its mirror image or the mixture of racemates; with the proviso that the sum of n, m, and p does not exceed 3, with the proviso that y is always trans-vinylene when P equals O.

Examples of alkyl 1 to 6 carbon atoms, inclusive, are methyl, ethyl, propyl, butyl, pentyl and hexyl and isomeric forms thereof.

Also included in the invention are the individual stereoisomers, and a mixture of the isomers wherein alpha and beta isomer mixture is represented by the wavy lines in all formulas.

Further, alpha configurations are represented by a dashed line, and beta configurations are represented by a thick line, in all formulas.

The specific assay used to detect gastric antisecretory activity is described as follows:

Adult female beagle dogs weighing 13–20 kg. are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1 N sodium hydroxide to pH 7.0. Following a 30 minute basal secretion the dogs are infused with a saline solution of histamine dihydrochloride at a dose of 1.0 mg./hr. The volume of the diffusion is kept at approximately 13 ml./hr. A steady state plateau of gastric secretion is obtained approximately 1 hour following the start of histamine infusion, at the end of which time the test compound dissolved in an ethanolic iso-osmotic phosphate buffer solution is administered by a single intravenous injection. The duration of the anti-secretory effects is determined and the side-effects, if any, recorded. The compound is rated active if statistically significant inhibition of secretory parameters occur following compound treatment.

By virtue of this anti-gastric secretory activity the compounds of formula I are useful in treating symptoms in humans and animals. A physican or veterinarian of ordinary skill could readily determine a subject who is exhibiting symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally, vaginally in such forms as suppositories or bougies; they may also be introduced in the form of eye drops, interparentally, subcutaneously, or intramuscularly, using forms known to the pharmaceutical art. In general the preferred form of administration is oral.

An effective but non-toxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration and the particular compound employed. An ordinarily skilled physician or veterinarian will readily determine and prescribe the effective amount of the anti-gastric secretory agent to prevent or arrest the progress of the condition. In so proceeding, the physician or veterinarian could employ relatively low dosages at first, subsequently increasing the dose until a maximum response is obtained.

Initial dosages of the compounds of the invention are ordinarily in the area of 0.1 µg/kg up to at least 4 µg/kg orally. When other forms of administration are employed equivalent doses are administered.

The compounds of this invention can also be administered as pharmacologically acceptable alkali metal salts such as lithium, sodium and potassium and the like. Additionally, the compounds of this invention may be administered in a suitable hydrated form.

Stating materials suitable for use in the manufacture of the compounds of the present invention are the cyclopent-1-ene alkenoic acids and esters of formula III of Chart A wherein n, R and X are as defined above; R' is a protecting group such as tri (lower alkyl) silyl, tetrahydropyranyl and tetrahydrofuranyl with tetrahydropyranyl being preferred, and q is an integer of from 2 to 4. The sum of n and q may not exceed 5.

The synthesis of the compound in which n=1 X=cis-vinylene, q=3 and R=CH$_3$ has been described by P. W. Collins et. al. in J. Med. Chem. 20, 1152(1977).

The manufacture of other cyclopent-1-ene alkanoic esters utilized in this invention is described in the Examples and is outlined in the scheme on Chart B.

Introduction of the oxygenated trans-vinyl side chain at the 2 position of the cyclopentane ring is effected by reaction with a suitable organocuprate reagent. The oxygenated trans-vinyl side chain groups are manufactured from the corresponding acetylenes by the process described by Pappo et. al. in Chemistry, Biochemistry and Pharmacological Activity of Prostanoids, p. 17–26, (1979). Example 2 describes the manufacture of a trans-vinyl stannane starting material from the corresponding acetylene.

Following the introduction of the lower side chain, the resulting prostaglandins are stereoselectively reduced to the corresponding F$_{2\alpha}$ analogs and are then suitably protected with a tri(lower alkyl) silyl group. (Examples 4 and 5).

Introduction of the second double bond is effected by formation of a phenylselenide derivative at carbon 2 of the prostaglandin followed by oxidation to the selenoxide which readily eliminates to give a 2, 3 trans double bond (Examples 6 and 7).

This double bond may be isomerized with lithium isopropylcyclohexylamide at low temperature to produce a mixture of 3, 4 cis and 3, 4 trans isomers (Example 10).

Conversion to the desired 9-keto compounds is carried out by selective hydrolysis of the C-9 protecting group followed by oxidation of the freed hydroxy group to the corresponding ketone and finally removal of the C-11 protecting group. (Examples 8 and 9)

Separation of the mixture of cis and trans isomers at C 3–4 may be effected by high pressure liquid chromatography.

When a resolved lower side chain is substituted for racemic lower side chain there is formed a mixture of diastereoisomers. This mixture of diastereoisomers may then be chromatographed to afford the individual stereoisomers.

The invention will appear more fully from the examples which follow. These examples are given by way of illustration only and are not to be construed as limiting the invention either in spirit or in scope as many modifications both in materials and in methods will be apparent from this disclosure to those skilled in the art. In these examples temperatures are given in degrees centigrade (°C.) and quantities of materials in grams and milliliters unless otherwise noted.

DESCRIPTION OF THE PREFERRED EMBODIMENTS

Example 1

Methyl 7-(3(RS)-tetrahydropyran-2-yloxy-5-oxocyclopent-1-ene)hept-5-cis enoate

To a solution of 2.88 g of methyl 4-(3(RS) hydroxy-5-oxocyclopent-1-ene) hept-5-cis-enoate in 36 ml of ether is added 50 mg of p-toluenesulfonic acid and 1.1 g of dihydropyran. The reaction mixture is allowed to stand at room temperature for about 24 hours, then is diluted with ether, washed successively with 5% aqueous potassium carbonate and water, dried over anhydrous sodium sulfate and stripped of solvent under reduced pressure. The residue is chromatographed on silica gel using 25% ethyl acetate in hexane as eluent to produce title compound.

Example 2

Trans vinylstannane 2.12 Grams of 4(RS)-trimethylsiloxy-4-methyl-1-octyne and 3.0 grams of tri-n-butyltin hydride are mixed and irradiated under argon with a sunlamp at 0° C. for 2 hours and then at 55° C. for 2 hours. The resulting title compound is used directly in Example 3.

Example 3

Racemic methyl 7-[3α-tetrahydropyran-2-yloxy-2β-(4(RS)-4-trimethylsilyloxy-4-methyl-1-trans-octenyl)-5-oxocyclopentane]-1α-hept-5-cis-enoate having formula XXI of Chart C 5 Grams of the trans vinylstannane product of Example 2 is dissolved in 15 ml of dry tetrahydrofuran, cooled to −60° under argon and treated with 4.35 ml of a 2.3 molar solution of n-butyl lithium in hexane. This solution is stirred at −60° for about 1 hour and is then treated with a solution of 1.31 g of copper 1-pentynilide and 3.2 g hexamethyl phosphorus triamide in 15 ml of ether. This solution is stirred for 15 minutes and then 2 g of the product of Example 1 in 15 ml of ether is added dropwise. After about 1 hour, the solution is poured into a mixture of ether and 1N hydrochloric acid. The ether layer is separated, washed with water twice, filtered, dried over sodium sulfate and stripped of solvent. The residue is chromatographed on silica gel using 15% ethyl acetate in hexane as eluent to give the title product.

Example 4

Racemic methyl 7-[3α-tetrahydropyran-2-yloxy-2β-(4(RS)-4-trimethylsilyloxy-4-methyl-1-trans-octenyl)-5αhydroxycyclopentane]-1α-hept-5-cis-enoate having formula XXII of Chart C 2.3 Grams of the product of Example 3 is dissolved in 40 ml of dry tetrahydrofuran, cooled to −60° under argon and treated dropwise with 9.2 ml of a 0.5 molar solution of lithium perhydro-9-b-boraphenalylhydride. The reaction mixture is stirred at −60° for 30 minutes after the addition is complete and then is poured into a mixture of ether and water. The organic layer is separated, washed with water, dried over anhydrous sodium sulfate and stripped of solvent under reduced pressure. The residue is chromatographed on silica gel with 20% ethyl acetate in hexane as eluent to give the title product.

Example 5

Racemic methyl 7-[3α-tetrahydropyran-2-yloxy-2β-(4(RS)-4-trimethylsilyloxy-4-methyl-1-trans-octenyl)-5α-triethylsilyoxycyclopentane]-1α-hept-5-cis-enoate having formula XXIII of Chart C 1.2 Grams of the product from Example 4 is dissolved in 10 ml of dimethylformamide and treated at room temperature with 300 mg of imidazole and then with 500 mg of triethylchlorosilane. The reaction mixture is stirred at room temperature for 10–15 minutes and then is poured into a mixture of ether and water. The organic layer is separated, washed with water 3 times, dried over anhydrous sodium sulfate and stripped of solvent under reduced pressure. The residue is chromatographed on silica gel using 10% ethyl acetate in hexane as eluent to give the title product.

Example 6

Formula XXIV of Chart C

To a solution of 169 mg of isopropylcyclohexylamine in 3 ml of dry tetrahydrofuran at −60° under argon is added 0.52 ml of a 2.3 molar solution of n-butyl lithium in hexane. After stirring for approximately 1 hour, this solution is treated dropwise over a 1 hour period with a solution of 650 mg of the produce from Example 5 in 3 ml of dry tetrahydrofuran. After 15 minutes of additional stirring, a solution of 312 mg of diphenyl diselenide in 1 ml of dry tetrahydrofuran is added dropwise. 15 Minutes after the addition is complete, the solution is allowed to come to 0° and then is poured into a mixture of ether and water. The organic layer is washed 2 times with water, dried over anhydrous sodium sulfate and stripped of solvent under reduced pressure. The residue is chromatographed on silica gel using 5% ethyl acetate in hexane as eluent to give the title product.

Example 7

Racemic methyl 7-[3αtetrahydropyran-2-yloxy-2β-(4(RS)-4-trimethylsilyloxy-4-methyl-1-trans-octenyl)-5α-triethylsilyloxycyclopentane]-1α-hept-2-trans-5-cis-dienoate having formula XXV of Chart C A solution of 570 mg of the product from Example 6 in 25 ml of ethanol is treated dropwise with stirring at room temperature with a solution of 1.1 g of sodium periodate in 12 ml of water and 25 ml of ethanol. The reaction mixture is allowed to stir for 3 hours after the addition is complete after which it is poured into a mixture of ether and water. The organic layer is washed with water, dried over sodium sulfate and stripped of solvent. The residue is chromatographed on silica gel using 5% ethyl acetate in hexane as eluent to give the title product.

Example 8

Formula XXXI of Chart D

A solution of 470 mg of the product from Example 7 in about 5 ml of a 3:1:1 mixture of acetic acid; water and tetrahydrofuran is stirred for 15–20 minutes at room temperature and then is poured into a mixture of ether and water. The organic layer is separated and washed with water 3 times, dried over sodium sulfate and stripped. The resulting product having the formula XXXI of Chart D is used directly is Example 9.

Example 9

Racemic methyl 7-[3α hydroxy-2β-(4(RS)-4-hydroxy-4-methyl-1-trans-octenyl)-5-oxocyclopentane]-1α hept-2-trans-5-cis-dienoate having formula XXXII of Chart D The product from Example 8 is dissolved in about 6 ml of methylene chloride and is treated at room temperature with stirring with about 150 mg of pyridinium chlorochromate. The reaction mixture is stirred for 1 hour, and is then poured into a mixture of ether and water. The organic layer is washed with water twice, filtered, dried over sodium sulfate and stripped of solvent. The residue is dissolved in a 3:1:1 mixture of acetic acid:water:tetrahydrofuran and kept at room temperature for 18–24 hours. The solution is diluted with ether and washed 3–4 times with water, dried over sodium sulfate and stripped of solvent. The residue is chromatographed on silica gel using 100% ethyl acetate as eluent to give the title product.

Example 10

Racemic methyl 7-[3α-tetrahydropyran-2-yloxy-2β-(4(RS)-4-trimethylsilyloxy-4-methyl-1-trans-octenyl)-5α triethylsilyloxycyclopentane]-1α-hept-3cis/trans-5-cis-dienoate having formula XXXIII of Chart D To a −30° solution of 104 mg of isopropylcyclohexylamine in 4 ml of dry tetrahydrofuran is added 144 mg of hexamethylphosphoric triamide followed by 0.32 ml of a 2.3 molar solution of n-butyl lithium in hexane. After stirring about 1 hour at −30°, the solution is cooled to −60° and a solution of 470 mg of the product from Example 7 in 5 ml of dry tetrahydrofuran is added dropwise over a 1 hour period. Approximately 15 minutes after the addition is completed, the reaction mixture is quenched with a solution of 3 drops of acetic acid in 1 ml of tetrahydrofuran. The reaction mixture is poured into a mixture of ether and water. The organic layer is separated, washed with water, dried over sodium sulfate and stripped of solvent. Chromatography of the residue on silica gel using 10% ethyl acetate in hexane as eluent gives the title product.

Example 11

When the product of Example 10 is substituted in Examples 8 and 9, there is obtained an approximately 1:1 mixture of racemic methyl 7-[3α-hydroxy-2β-(4(RS)-4-hydroxy-4-methyl-1-trans-octenyl)-5-oxocyclopentane]-1α hept-3-trans-5-cisdienoate having formula XXXIV of Chart D and racemic methyl 7-[3α-hydroxy-2β-(4(RS)-4-hydroxy-4-methyl-1-trans-octenyl)-5-oxocyclopentan]-1α-hept-3-cis-5-cis-dienoate formula XXXV of Chart D.

Example 12

When the mixture of products of Example 11 is subjected to high pressure liquid chromatography using a Lichrosorb Si 60 column and a mobile phase consisting of 97% of 2,2,4-trimethyl pentane and 3% ethanol there is obtained as separate compounds racemic methyl 7(3α-hydroxy-2β-[4(RS)-4-hydroxy-4-methyl-1-trans-octenyl)-5-oxocyclopentane]-1α-hept-3-trans-5-cis-dienoate having formula XXXIV on Chart D and racemic methyl 7-[3α-hydroxy-2β(4(RS)-4-hydroxy-4-methyl-1-trans-octenyl)-5-oxocyclopentane]-1α-hept-3-cis-5-cis-dienoate having formula XXXV of Chart D.

Example 13

Racemic methyl 7-[3α hydroxy-2β-(4(RS)-4-hydroxy-4-methyl-1-trans-octenyl)-5-oxocyclopentane]-1α-hept-3-trans-5-trans-dienoate having formula XLIII of Chart E A solution of 200 mg of the product from Example 10 in 4 ml of carbon tetrachloride containing 0.5 mg of iodine is exposed to indirect sunlight for approximately 24 hours. The solution is stripped of solvent and when the residue is substituted in Examples 8 and 9, there is obtained the title product.

Example 14

5-Bromo-2-pentanone ethylene ketal having formula XLIV of Chart E 4.0 grams of 5-chloro-2-pentanone ethylene ketal is mixed with 9.0 grams of lithium bromide and 2.0 grams of diisopropylethylamine in 30 ml of tetrahydrofuran which has been distilled from lithium aluminum hydride. The mixture is refluxed under nitrogen for 48 hours, cooled and poured into a mixture of ether and water for extraction. The ether layer is washed twice with water, then with 1 N hydrochloric acid and then twice again with water. The ether layer is then dried over sodium sulfate and evaporated under reduced pressure to give title product.

Example 15

2-Tetrahydropyranyl-4-pentynyl ether having formula XLV of Chart E 0.1 grams of p-toluenesulfonic acid is added to a stirred mixture of 4.2 grams 4-pentyn-1-ol and 5.0 grams dihydropyran. After about 30 minutes, the mixture is treated with 0.5 g. of triethylamine and vacuum distilled to give the title product.

Example 16

Decynyl ketal of formula LI of Chart F

A solution containing 18.5 grams of 2-tetrahydropyranyl-4-pentynyl ether of Example 14 in 125 ml of tetrahydrofuran which has been freshly distilled from lithium aluminum hydride is cooled to approximately −30° C. and treated with 46 ml of 2.4 molar n-butyl lithium solution in hexane. The solution is allowed to come to room temperature. After approximately 30 minutes at room temperature, 21 g. of 5-bromo-2-pentanone ethylene ketal of Example 13 is added, followed by addition of 30 ml of hexamethylphosphoric triamide, with stirring. After 1 hour the reaction mixture is poured into a mixture of ether and 1 N hydrochloric acid. The ether layer is washed with water, dried over sodium sulfate and stripped of solvent in vacuo to give the title product, as a colorless, viscous liquid.

Example 17

30 Grams of the decynyl ketal of Example 15 is dissolved in a mixture of 150 ml of 1 N hydrochloric acid, 200 ml of tetrahydrofuran and 50 ml of methanol. The solution is maintained at room temperature for 48 hours and then refluxed for 5-6 hours. The solution is then cooled to room temperature and solid potassium carbonate is added until the pH reaches 7. The solution is then stripped to ½ of its volume, diluted with water and extracted with ether twice. The ether extracts are combined, washed with water, dried over sodium sulfate and stripped of solvent to give 9-oxodec-4-yn-1-ol which is used without pruification in Example 14.

EXAMPLE 18

9-Oxodec-4-ynoic acid

20 Grams of 9-oxodec-4-yn-1-ol of Example 16 is dissolved in 200 ml of acetone and cooled to 0° C. The cold solution is stirred and treated dropwise with 90 ml of 2.67 molar Jones reagent (chromic acid in sulfuric acid and water). The acetone solution is decanted from the solid chromium salts, which are then rinsed with fresh acetone. The acetone solutions are combined and poured into a mixture of ether and water. The ether layer is separated from the water, washed once with water, and then extracted three times with 5% potassium carbonate solution. The alkaline extracts are combined, acidified with concentrated hydrochloric acid and extracted twice with ether and once with ethyl acetate. The extracts are combined, dried over sodium sulfate, and stripped of solvent to give the pure title product.

Example 19

Cis-9-oxodec-4-enoic acid

10 Grams of the 9-oxodec-4-ynoic acid of Example 18 is hydrogenated at room temperature in toluene containing about 0.5% quinoline with 5% palladium on barium sulfate as catalyst. The toluene solution is washed with 1 N hydrochloric acid, then water. The solution is dried over sodium sulfate and stripped of solvent to give, as a yellow oil, the title product.

Example 20

7-(2,3,5-Trioxo-4-methoxalylcyclopentane)hept-4-cis-enoic acid having formula LII of Chart F 3.2 Grams of potassium metal is added to 50 ml of t-butyl alcohol and refluxed under argon. After the potassium has dissolved, a solution of 2.52 g. of cis-9-oxodec-4-enoic acid and 4.85 g. of dimethyloxalate, which has been recrystallized from hexane in 25 ml of t-butyl alcohol is added dropwise to the refluxing solution over a one hour period. The reaction mixture is refluxed for 2 hours more, cooled to room temperature and filtered under argon to give an orange cake. The orange filter cake is added to give a mixture of chloroform and 1 N hydrochloric acid. The chloroform layer is washed with a saturated sodium chloride solution, dried over sodium sulfate and stripped of solvent to give the title product, and its various tautomeric enol forms.

Example 21

7-(2,3,5-trioxocyclopentane) hept-4-cis-enoic acid having formula LIII of Chart F 4.0 Grams of the 7-(2,3,5-trioxo-4-methoxalylcylopentane) hept-4-cis-enoic acid of Example 20 is added to 100 ml of 1 N hydrochloric acid and refluxed under argon for 3 hours. The solution is cooled to room temperature, filtered and extracted twice with saturated sodium chloride solution, dried and stripped of solvent to give a red oil. The red oil is chromatographed on silica gel (60% ethyl acetate, 39% hexane and 1% acetic acid as eluent) to give the title product and its various tautomeric enol forms as a yellow solid melting at 78°–80°.

Example 22

(±)7-(2,5-dioxo-3-hydroxycylopentane) hept-4-cis-enoic acid having the formula LIV of Chart F 1.15 Gram of 7(2,3,5-trioxocyclopentane) hept-4-cis-enoic acid is dissolved in 35 ml of ethanol and 30 ml of water and cooled to 0° C. 0.55 g of sodium borohydride is dissolved in 5.0 ml by volume of water and added dropwise to the ethanol solution. After the addition is complete, the solution is stirred at 0° C. for 30 minutes. The solution is poured into ethyl acetate and 1 N hydrochloric acid. The aqueous layer is extracted three times with additional ethyl acetate. The ethyl acetate extracts are combined, washed once with saturated sodium chloride, dried over sodium sulfate and stripped of solvent to give the title product, and its various enol forms as a viscous yellow oil.

Example 23

(±) methyl 7-(4-hydroxy-2-methoxy-5-oxocyclopent-1-ene) hept-4-cis-enoate, having formula LV of Chart F To a solution of 2.0 g of (±)7-(2,5-dioxo-3-hydroxycylopentane)hept-4-cis-enoic acid in 30 ml of dry methanol is added 10 ml of 2, 2-dimethoxypropane and 4 ml of 1% methanolic hydrogen chloride. The mixture is allowed to stand at room temperature for 48 hours and is then stripped to dryness at room temperature under reduced pressure. About 4 ml of ether is added and the mixture is allowed to stand at room temperature for an additional 48 hours. The solidified mixture is taken up in toluene containing 1% triethylamine, and the solution is washed successively with dilute potassium carbonate and water, dried over sodium sulfate and stripped of solvent. The residue is recrystallized from ether to give, as a white solid melting at 82°–84° C., the title product.

Example 24

(±) methyl 7-(3-hydroxy-5-oxocyclopent-1-ene) hept-4-cis-enoate having formula LXI of Chart G 100 ml of dry toluene are placed in a three-neck flask and cooled to −70° C. in an isopropyl alcohol-dry ice bath. In separate dropping funnels are placed 15.5 ml of 1.83 molar sodium dihydrobis-(2-methoxyethoxy)aluminate diluted with 100 ml of toluene and a solution of 6.92 of (±) methyl 7-(4-hydroxy-2-methoxy-5-oxocyclopent-1-ene) hept-4-cis-enoate in 200 ml of toluene. The two solutions are added dropwise and simultaneously to the flask. The temperature of the flask is not allowed to exceed −60° C. during the additions. The mixture is stirred at −70° C. for 3.5 hours and then at 0° for 15 minutes, quenched with a solution of 5.0 ml methanol in 10 ml of toluene, and acidified with 150 ml of 1 N hydrochloric acid. The organic layer is separated, washed with water, dried over sodium sulfate and stripped of solvent. The residue is chromatographed on silica gel (70% ethyl acetate, 30% hexane as eluent) to give the title product, as a viscous oil.

EXAMPLE 25

Racemic methyl 7-[3α-hydroxy-2β-(4(RS)-4-hydroxy-1-hept-2-trans-4-cis-dienoate] having formula LXII of Chart G When racemic methyl 7-(3-hydroxy-5-oxocyclopent-1-ene) hept-4-cis-enoate is substituted in Example 1, and carried through Examples 3,4,5,6,7,8 and 9 there is obtained the title product.

EXAMPLE 26

Racemic methyl 8-(3-tetrahydropyran-2-yloxy-5-oxocyclopent-1-ene)-oct-5-cis-enoate having formula LXIII of Chart G When 5-hexyn-1-ol is substituted in Example 15 and carried through Examples 16,17,18,19,20,21,22,23,24 and 1 there is obtained the title product.

EXAMPLE 27

(±) 4-Hydroxy-4-n-propyl-1-octyne

14 Grams of powdered (50 mesh) magnesium metal is suspended in 80 ml of ether and activated by addition of 200 mg of mercuric chloride. A solution of 38.4 g of 4-octanone and 36.6 g of propargyl bromide in 120 ml of ether and 50 ml of benzene is added dropwise at a rate which produced a gentle reflux. After the addition is complete, the reaction mixture is stirred for several hours and is then poured into 500 ml of cold 5% sulfuric acid. The organic layer is separated, washed with water twice, dried over sodium sulfate and stripped of solvent. The residue is distilled under vacuum to give the title product.

EXAMPLE 28

(±) 4-Trimethylsilyloxy-4-n-propyl-1-octyne 16.8 Grams of 4-hydroxy-4-n-propyl-1-octyne is dissolved in 100 ml of dimethylformamide and treated with 8 g of imidazole and then with 12 g of trimethylchlorosilane. The reaction mixture was stirred at room temperature for 1 hour and then poured into a mixture of ether and water. The organic layer was washed with water 3–4 times, dried over sodium sulfate, and stripped of solvent. Distillation of the residue gave the title product as a colorless liquid.

EXAMPLE 29

Racemic methyl 8-[3α hydroxy-2β-(4(RS)-4-hydroxy-4-n-propyl-1-trans-octenyl-5-oxocyclopentane-1α oct-2-trans-5-cis-dienoate having formula, LXIV of Chart G When (±) 4-trimethylsilyloxy-4-n-propyl -1-octyne is substituted into Example 2, there is obtained the corresponding trans-vinylstannane derivative.

When this trans-vinylstanne product is substituted with the product form Example 26 in Example 3 and the product thereof is carried through Examples 4,5,6,7,8 and 9, there is obtained the title product.

EXAMPLE 30

When the trans-vinylstanne product of Example 29 and the product from Example 26 are substituted in Example 3 and the product thereof is carried through Examples 4,5,6,7 and 10 and then substituted in Examples 8 and 9 there is obtained an approximately 1:1 mixture of racemic methyl 8-[3α-hydroxy-2β-(4(RS)-4-hydroxy-4-n-propyl-1-trans octenyl)-5-oxocyclopentane]1α-oct-3-trans-5-cis-dienoate having formula LXV of Chart G and racemic methyl 8-[3α-hydroxy-2β-(4(RS)-4-hydroxy-4-n-propyl-1-trans-octenyl)-5-oxocyclopentane]-1-oct-3-cis-5-cis-dienoate having the formula LXVI of Chart G.

EXAMPLE 31

4-Bromo-2-butanone

70 Grams of methyl vinyl ketone is dissolved in 400 ml of ether and cooled to 0°. Anhydrous hydrogen bromide is bubbled in slowly until approximately 86 g is absorbed. The flask is stoppered and left at room temperature overnight. The solution is stripped of solvent and the residue distilled under reduced pressure to give the title product.

EXAMPLE 32

4-Bromo-2-butanone ethylene ketal

A mixture of 75 g of 4-bromo-2-butanone, 40 g of ethylene glycol, 250 mg of p-toluenesulfonic acid acid and 500 ml of toluene is refluxed for about 4-6 hours under a Dean-Stark water trap. The mixture is cooled, poured into ethyl acetate and dilute potassium carbonate solution. The organic layer is separated, washed with water, dried over sodium sulfate, stripped of solvent and the residue is distilled under reduced pressure to give the title product.

Example 33

Racemic methyl 6-(3-tetrahydropyran-2-yloxy-5-oxocyclopent-1-ene) hex-4-cis-enoate having formula LXXI of Chart H When 4-bromo-2-butanone ethylene ketal is substituted into Example 16, and carried through Examples 17-24, and then Example 1, there is obtained the title product.

Example 34

1-Nonyn-4-ol

When 1-hexanal is substituted for 4-octanone in Example 27, there is obtained the title product.

Example 35

1-Nonyn-4-one

A solution of 14 g of 1-nonyn-4-ol in 100 ml of acetone is cooled to 0° and treated dropwise with 70 ml of 2.67 molar Jones reagent with stirring. The reaction mixture is poured into a mixture of hexane and water, the organic layer is separated and washed with water, dried over sodium sulfate, stripped of solvent, and the residue distilled to give the title product.

EXAMPLE 36

4-Vinyl-1-nonyn-4-ol

A solution of 130 ml of 2.3 molar vinyl magnesium chloride in 100 ml of ether is cooled to 0° and treated dropwise with 14 g of 1-nonyn-4-one in 50 ml of ether. The reaction mixture is allowed to come to room temperature and poured into ether and dilute hydrochloric acid. The organic layer is separated, washed with water, dried over sodium sulfate, stripped of solvent and the residue is chromatographed on silica gel with 20% ethyl acetate in hexane as eluent to give the title product.

Example 37

Trans vinyl stannane, formula LXXII of Chart H

When 4-vinyl-1-nonyn-4-ol is substituted into Example 28 and then Example 2 there is obtained the title product.

Example 38

Racemic methyl 6-[3α-hydroxy-2β-(4(RS)-4-hydroxy-4-vinyl-1-trans-nonenyl)-5-oxo-cyclopentane]-1α-hex-2-trans-4-cis-dienoate, formula LXXIII of Chart H When the products of Examples 33 and 37 are substituted in Example 3 and carried through Examples 4,5,6,7,8 and 9 there is obtained the title product.

Example 39

When 4-bromo-2-butanone ethylene ketal and the tetrahydropyranyl ether of 5-hexyn-1-ol are substituted in Example 16, there is produced the ketal-ether having formula LXXIV of Chart H.

Example 40

1 Gram of lithium metal is added to 150 ml of anhydrous ammonia in a 3-necked flask fitted with a dry ice condenser and immersed in a dry ice-isopropanol bath. 15 Grams of the product from Example 39 and 5 ml of t-butanol are mixed and added dropwise to ammonia solution. The reaction mixture is stirred for 2 hours after the addition is complete. The flask is removed from the ice bath and the reaction mixture is quenched with solid ammonium chloride. Ether is then added dropwise allowing the ammonia to evaporate. The solution is poured into ether and dilute hydrochloric acid. The ether layer is separated, washed twice with dilute hydrochloric acid, then water, dried over sodium sulfate and stripped of solvent to give the product having formula LXXV of Chart H.

Example 41

Racemic methyl
7-[3α-hydroxy-2β-(4(RS)-4-hydroxy-4-methyl-1-trans-
octenyl)-5-oxocyclopentane]-1α-hept-2-trans-5-trans-
dienoate, formula LXXVI of Chart H When the product from Example 40 is substituted in Example 17 and carried through Example 18,20,21,22,23,24,1,3,4, 5,6,7,8 and 9 there is obtained the title product.

Example 42

Isopropyl 7-(3(RS)-hydroxy-5-oxocyclopent-1-ene) hept-5-cis-enoate having formula LXXXI of Chart I Methyl 7-(3(RS)-hydroxy-5-oxocyclopent-1-ene hept-5-cis-enoate (500 mg) is dissolved in 7 ml of acetone and treated with 7 ml of one N hydrochloric acid. The mixture is allowed to stand at room temperature for 48 hours. The solution is stripped under reduced pressure to remove most of the acetone. The aqueous solution is extracted several times with ethyl acetate. The extracts are combined, washed once with saturated sodium chloride solution and dried over sodium sulfate and then stripped again to yield the cyclopentenoic acid.

A solution of the cyclopentenoic acid (500 mg) and imidazole (600 mg) in 8 to 10 ml of dimethylformamide (DMF) is treated at room temperature with stirring with 800 mg of t-butyl dimethyl silyl chloride. After one hour, the reaction mixture is poured into a one to one mixture of hexane/ether and water. The organic layer is washed with water three times, dried over sodium sulfate, and stripped to yield an oil. Chromatography using a 10% ethyl acetate 90% hexane solvent system on silica gel gives 600 mg of pure product, a bis silyl ether. 600 mg of this silyl ether is dissolved in about five ml of methylene chloride and then cooled to 0° in an ice bath. It is then treated with two to three drops of (DMF) and then with oxalyl chloride (200 mg) in one ml of methylene chloride. The reaction mixture is allowed to come to room temperature. After one hour the solution is treated with about 1 ml of dry isopropanol. The reaction mixture is stirred at room temperature for 30 minutes, then diluted with ether and washed with water 3 times, dried over sodium sulfate and stripped of solvent to give the title product.

Example 43

Racemic isopropyl
7-[3α-hydroxy-2β-(4(RS)-4-hydroxy-4-methyl-1-trans-
octenyl)-5-oxocyclopentane]-1α-hept-2-trans-5-cis-
dienoate, formula LXXXII of Chart I When the product of Example 42 is substituted in Example 1 and carried through Examples 3,4,5,6,7,8 and 9, there is obtained the title product.

Example 44

Racemic
7-[3α-hydroxy-2β-(4(RS)-4-hydroxy-4-methyl-1-trans-
octenyl)-5-oxocyclopentane]-1-hept-2
trans-5-cis-dienoic acid, formula LXXXIII of Chart I 100 mg of racemic methyl 7-[3α-hydroxy-2β-(4(RS)-4-hydroxy-4-methyl-1-trans-octenyl)-5-oxocyclopentane]-1-hept-2-trans-5-cis-dienoate is dissolved in 5 ml of 95% ethanol and added to 30 ml of a 7.8 pH TRIS(2-amino-2-hydroxymethyl-1-,3-propanediol) buffer. This mixture is treated with 15 mg of hog liver esterase (Sigma Chemical Co. No. E-3128) and stirred for 3 to 4 hours at room temperature. The mixture is diluted with ether, washed with 1 N hydrochloric acid, then water, dried over sodium sulfate and stripped of solvent. The residue is chromatographed on silica gel (100% ethyl acetate as eluent) to give the title product.

EXAMPLE 45

2.12 Grams of (4S)-4-trimethylsilyloxy-4-methyl-1-octyne which was obtained by the method described in "Recent Developments in the Synthesis of Antisecretory Prostaglandins", R. Pappo et. al. in *Chemistry, Biochemistry and Pharmacological Activity of Prostanoids*, 1979 and 3.0 grams of tri-n-butyltin hydride are mixed and irradiated under argon with a sunlamp at 0° for 2 hours and then at 55° for 2 hours. The resulting product is used directly in Example 46.

Example 46

When the product of Example 45 is substituted into Example 3 and carried through Examples 4,5,6,7,10,8 and 9, there is obtained a mixture of diastereoisomers which are separated by chromatography on hydroxyapatite (6% n-butanol, 94% cyclohexane) to give the products methyl 7[3(S)-hydroxy-2β-4(S)-hydroxy-4-methyl-1-trans-octenyl)-5-oxocyclopentane]-1-hept-3 trans/cis (1:1)-5-cis -dienoate having formula LXXXIV of Chart I and methyl 7-(3(R)-hydroxy-2β-4(S)-hydroxy-4-methyl-1-trans-octenyl)-5-oxocyclopentane]-1α-hept-3-trans/cis (1:1)-5-cis-dienoate having formula LXXXV of Chart I.

When the latter mixture of products is subjected to high pressure liquid chromatography using a Lichrosorb Si 60 column and a mobil phase consisting of 97% 2,2,4-trimethylpentane and 3% ethanol there is obtained as separate compounds methyl 7-[3(R)-hydroxy-2β-4(S)-hydroxy-4-methyl-1-trans-octenyl)-5-oxocyclopentane]-1α-hept-3-trans-5-cis-dienoate having formula XCI of Chart J and methyl 7-[3(R)-hydroxy-2β-4(S)-hydroxy-4-methyl-1-trans-octenyl)-5-oxocyclopentane]-1-hept-3-cis-5-cis-dienoate having formula XCII of Chart J.

Example 47

(±) 4-trimethylsilyloxy-4-trifluoromethyl-1-octyne, formula XCIII of Chart J

When n-butyltrifluoromethyl ketone (prepared by procedure of H. F. Bluhm et al, *J. Am. Chem. Soc.* 77 4406 (1955) is substituted into Example 27 and carried through Example 28, there is obtained the title product.

Example 48

When (±) 4-trimethylsilyloxy-4-trifluoromethyl-1-octyne is substituted into Example 2, there is obtained the corresponding trans-vinylstannane derivative. When this trans-vinylstannane product is substituted into Example 3 and the product thereof is carried through Examples 4,5,6,7,10,8 and 9, there is obtained an approximately 1:1 mixture of racemic methyl 7-[3α-hydroxy-2β-(4(RS)-4-hyroxy-4-trifluoromethyl-1-trans-octenyl) 5-oxocyclopentane]-1-hept-3-trans-5-cis-dienoate having the formula XCIV of Chart J and racemic methyl 7-[3α-hydroxy-2β-(4(RS)-4-hydroxy-4-trifluoromethyl-1-trans-octenyl)-5-oxocyclopentane]-1α-hept-3-cis-5-cis-dienoate having the formula XCV of Chart J.

Example 49
Racemic methyl 7-[3α-hydroxy-2β[4(RS)-4 hydroxy-4-methyl-1-trans-octenyl]-5-oxocyclopentane-1α]-hept-3 cis-5-trans.
Using the product from example 40 in Example 17 and using the process in examples 18-24 followed by 1,3,4,5,6,7,10,8 & 9 the title product is formed.
CHART A
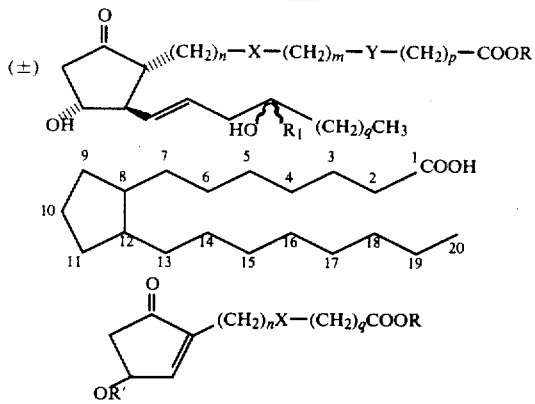
CHART B
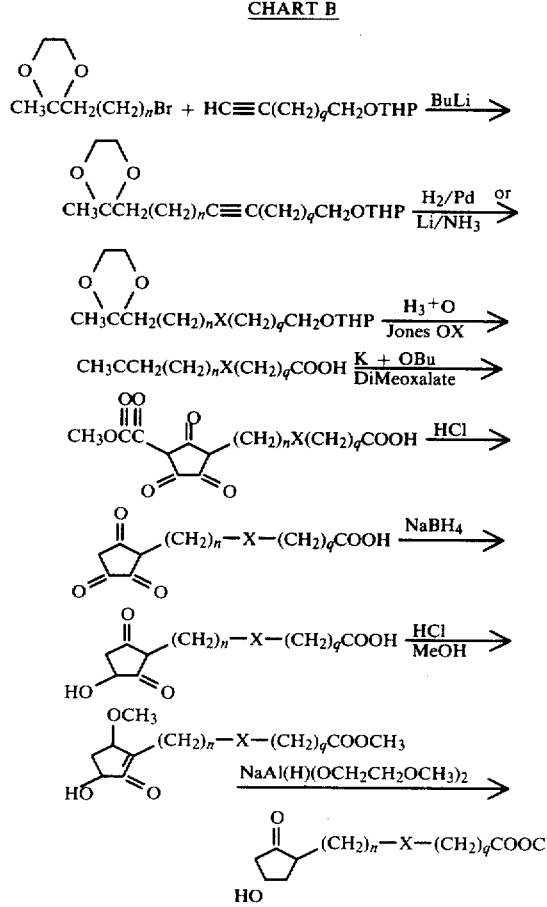
CHART C
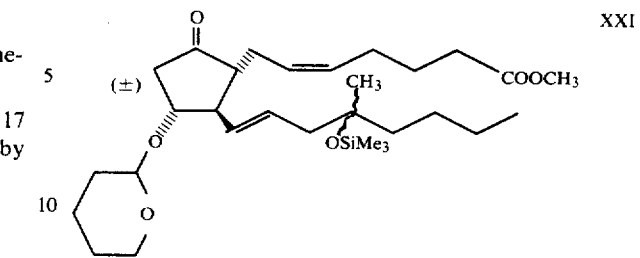
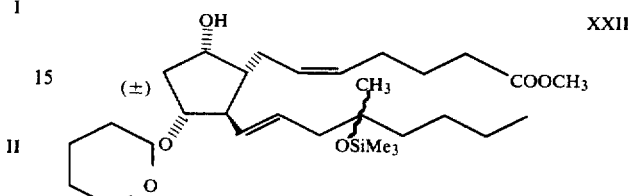
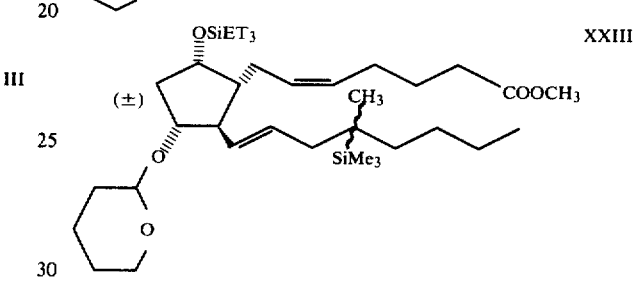
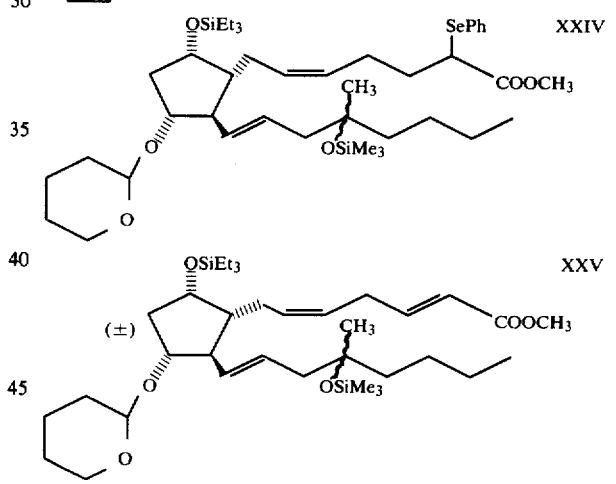
CHART D
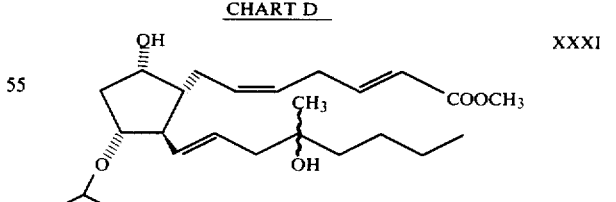
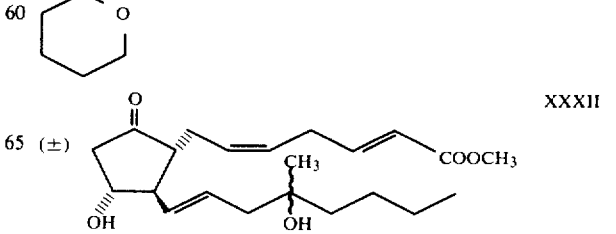

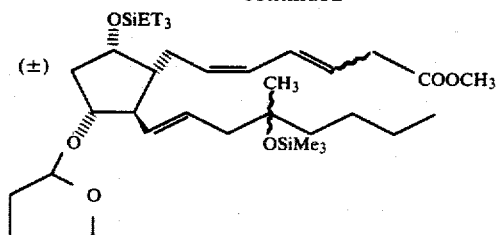
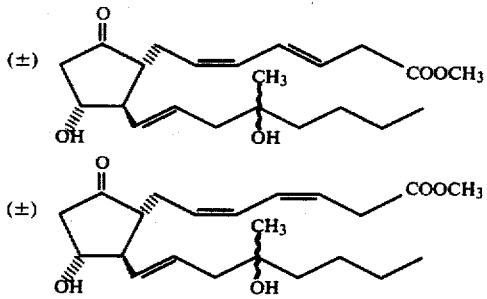
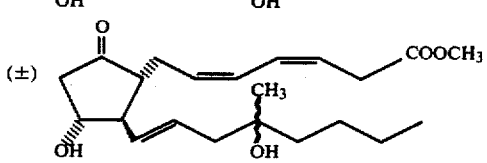
CHART E
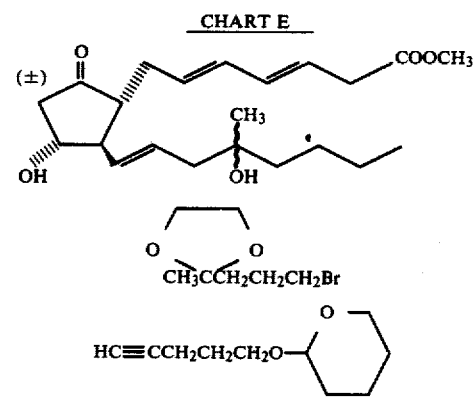
CHART F
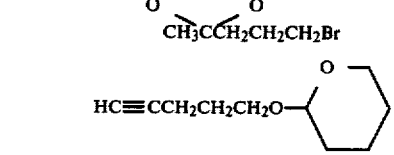
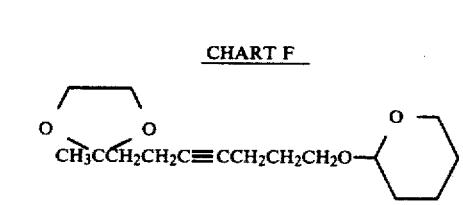
CHART G
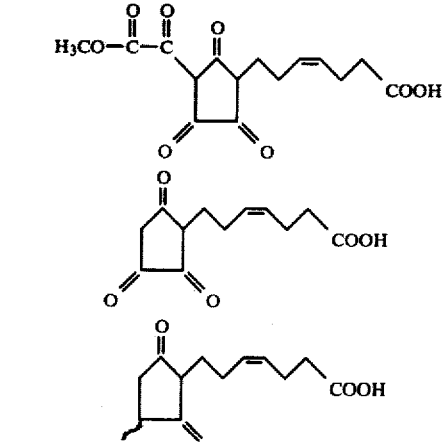
CHART H
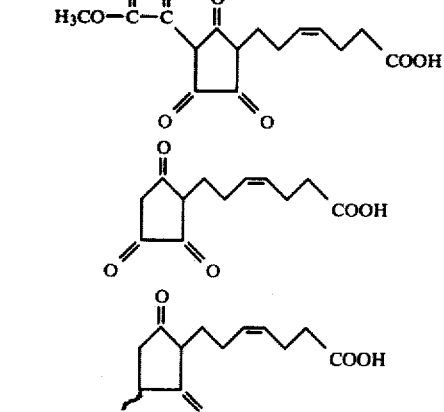

19
-continued

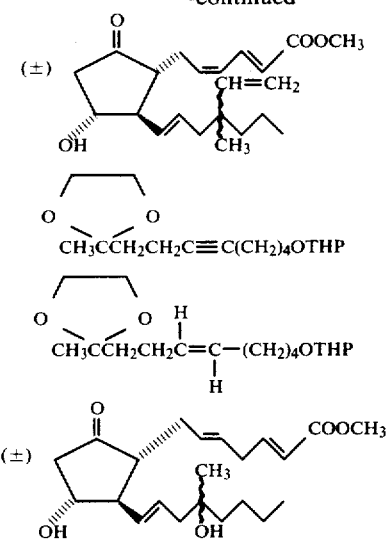

CHART I

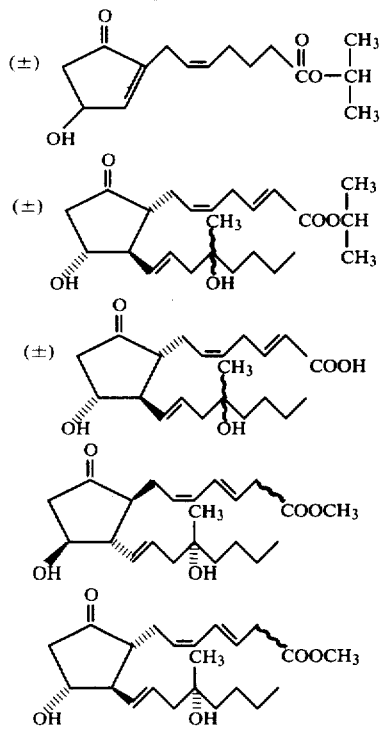

CHART J

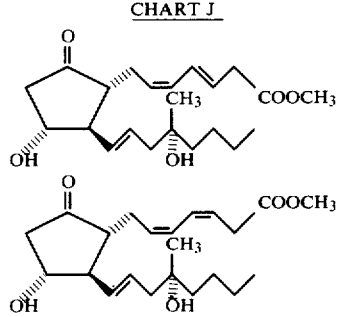

20
-continued

LXXIII

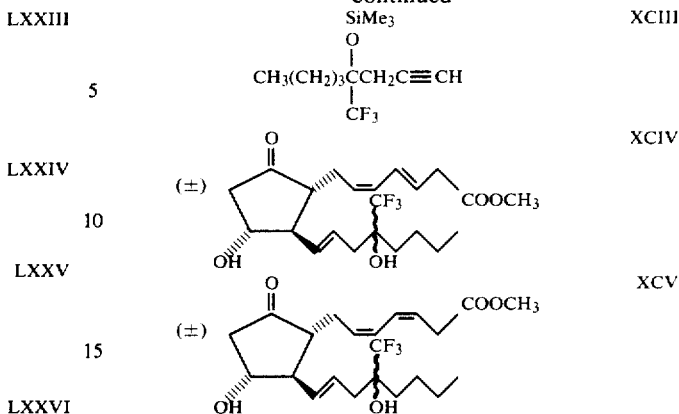

LXXIV

LXXV

LXXVI

I claim:
1. A compound according to the formula

LXXXI

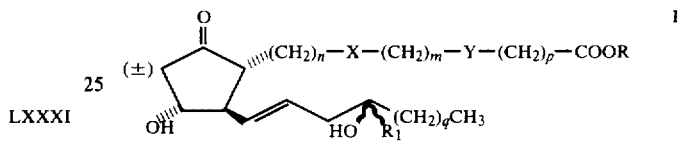

wherein n is an integer from 1 through 3 inclusive;
wherein m+p are integers from 0 through 2 inclusive, m and p being either the same or different; wherein q is an integer of from 2 through 4 inclusive; wherein X and Y are cis or trans vinylene, X and Y being either the same or different; wherein R is:

LXXXII (a) hydrogen; or
(b) alkyl of 1 to 6 carbon atoms inclusive;
wherein $R_1$ is:

LXXXIII (a) hydrogen;
(b) alkyl of 1 to 6 carbon atoms inclusive;
(c) vinyl;
(d) ethynyl;
(e) cyclopropyl;

LXXXIV (f) —$CH_2Z$;
(g) —$CH(Z)_2$; or
(h) —$CZ_3$;
wherein Z is:
(a) chlorine; or
(b) fluorine; and

LXXXV wherein the (±) refers to the structure of formula I, its mirror image or the mixture of racemates; with the proviso that the sum of n, m, and p does not exceed 3; with the proviso that y is always trans-vinylene when p equals 0.

2. A compound according to claim 1 wherein X is cis vinylene.

3. A compound according to claim 2 wherein n is an integer from 1 through 2 inclusive; wherein m and p are the integers 0 through 1 inclusive, m and p being either the same or different.

XCI

4. A compound according to claim 3 wherein $R_1$ is methyl.

5. Racemic methyl 7-[3α hydroxy-2β [4(RS)-4-hydroxy-4-methyl-1-trans-octenyl)-5-oxocyclopentane]-1α-hept-3-trans-5cis-dienoate and racemic methyl 7-[3α-hydroxy-2β [4(RS)-4-hydroxy-4-methyl-1-trans-octenyl)-5-oxocyclopentane]-1hept-3-cis-5-cis-dienoate in an approximately 1 to 1 mixture, a compound according to claim 4.

XCII

6. Racemic methyl 7-[3α-hydroxy-2β [4(RS)-4 hydroxy-4-methyl-1-trans-octenyl)-5-oxocyclopentane]-1α-hept-3-trans-5-cis-dienoate, a compound according to claim 4.

7. Racemic methyl 7[3α-hydroxy-2β-4(RS)-4-hydroxy-4-methyl-1-trans-octenyl)-5-oxocyclopentane]-1α-hept-3-cis-5-cis-dienoate, a compound according to claim 4.

8. Racemic methyl 7-[3α-hydroxy-2β-(4(RS)-4-hydroxy-4-methyl-1-trans-octenyl)-5-oxocyclopentane]-1α-hept-2-trans-5-cis-dienoate, a compound according to claim 4.

9. Racemic methyl 7-[3α-hydroxy-2β-(4(RS)-4-hydroxy-4-methyl-1-trans-octenyl)-5-oxocyclopentene]-1α-hept-2 trans-4-cis-dienoate, a compound according to claim 4.

10. Racemic methyl 8-[3αhydroxy-2β[4(RS)-4-hydroxy-4-methyl-1-trans-octenyl)-5-oxocyclopentane]-1α-oct-3-trans-5-cis-dienoate, a compound according to claim 4.

11. Racemic methyl 6-[3α-hydroxy-2β [4(RS)-4-hydroxy-4-methyl-1-trans-octenyl)-5-oxocyclopentane]-1α-hex-2-trans-3cis-5-cis-dienoate.

12. A compound according to claim 1 wherein X is trans vinylene.

13. A compound according to claim 11 wherein n is an integer from 1 through 2, inclusive; wherein m and p are the integers 0 through 1 inclusive m and p being either the same or different.

14. A compound according to claim 12 wherein $R_1$ is methyl.

15. Racemic methyl 7-[3α-hydroxy-2β(4(RS)-4-hydroxy-4-methyl-1trans-octenyl]-5-oxocyclopentane-1α-hept-3-trans-5-trans-dienoate, a compound according to claim 14.

16. Racemic methyl 7-[3αhydroxy-2β[4(RS)-4-hydroxy-4-methyl-1-trans-octenyl]-5-oxocyclopentane-1αhept-3-cis-5-trans, a compound according to claim 14.

17. Racemic methyl 7-[3α-hydroxy-2β-(4(RS)-4-hydroxy-4-methyl-1-trans-octenyl)-5-oxocyclopentene]-1αhept-2trans-4-trans-dienoate, a compound according to claim 14.

18. Methyl 7-[3(R)-hydroxy-2β-4(S)-hydroxy-4-methyl-1-trans-octenyl)-5-oxocyclopentane]-1α-hept-3-trans-5-cis-dienoate, a compound according to claim 1.

19. Methyl 7-[3(R)-hydroxy-2β-4(S)-hydroxy-4-methyl-1-trans-octenyl)-5-oxocyclopentane]-1α-hept-3-cis-5-cis-dienoate, a compound according to claim 1.

* * * * *